(12) United States Patent
Steinboeck et al.

(10) Patent No.: US 8,491,185 B2
(45) Date of Patent: Jul. 23, 2013

(54) METHOD FOR MONITORING THE THERMAL COUPLING OF A MEASURING CELL

(75) Inventors: Wolf-Dietrich Steinboeck, Graz (AT); Robert Felsberger, Graz (AT); Michael Kraker, Graz (AT); Friedrich Schneider, Buch/Hartberg (AT); Juergen Walla, Graz (AT)

(73) Assignee: Roche Diagnostics Operations Inc., Indianapolis, IN (US)

( * ) Notice: Subject to any disclaimer, the term of this patent is extended or adjusted under 35 U.S.C. 154(b) by 763 days.

(21) Appl. No.: 12/635,478

(22) Filed: Dec. 10, 2009

(65) Prior Publication Data

US 2010/0158070 A1 Jun. 24, 2010

(30) Foreign Application Priority Data

Dec. 18, 2008 (EP) ..................... 08172121

(51) Int. Cl.
*G01N 25/00* (2006.01)
*G01N 25/18* (2006.01)

(52) U.S. Cl.
USPC .................. 374/44; 374/10; 374/4; 374/102; 374/57; 374/29

(58) Field of Classification Search
USPC ................. 374/1, 10, 11, 12, 4, 5, 29, 30, 43, 374/44, 45, 57, 100, 102, 103, 33, 31, 39, 374/147, 148, 163; 422/105, 108, 109, 51; 436/137
See application file for complete search history.

(56) References Cited

U.S. PATENT DOCUMENTS

| | | | |
|---|---|---|---|
| 3,372,588 A * | 3/1968 | Ziemke et al. ................... 374/29 |
| 4,686,479 A | 8/1987 | Young et al. | |
| 5,046,496 A | 9/1991 | Betts et al. | |
| 5,232,667 A | 8/1993 | Hieb et al. | |
| 5,329,804 A | 7/1994 | Germany et al. | |
| 5,653,539 A * | 8/1997 | Rosengaus ..................... 374/159 |
| 5,832,921 A | 11/1998 | Lennert et al. | |
| 6,663,278 B1 * | 12/2003 | Chien et al. ..................... 374/43 |
| 6,890,492 B1 * | 5/2005 | Turner et al. ..................... 506/33 |
| 6,890,757 B2 | 5/2005 | Kurkowski et al. | |
| 7,491,175 B2 | 2/2009 | Ruether et al. | |
| 8,042,993 B2 * | 10/2011 | Van Maanen ................... 374/43 |
| 2003/0057108 A1 | 3/2003 | Sridharan | |
| 2003/0066638 A1 * | 4/2003 | Qu et al. ......................... 165/186 |
| 2006/0140822 A1 * | 6/2006 | Krysl et al. ..................... 422/108 |
| 2007/0230535 A1 * | 10/2007 | Atwood et al. .................... 374/1 |
| 2007/0237202 A1 * | 10/2007 | Li ................................ 374/147 |
| 2010/0046574 A1 * | 2/2010 | Hamann et al. .................. 374/43 |
| 2011/0002356 A1 * | 1/2011 | Emanuel et al. ................. 374/44 |
| 2012/0069867 A1 * | 3/2012 | Wijffels ......................... 374/157 |

FOREIGN PATENT DOCUMENTS

| | | |
|---|---|---|
| EP | 0399227 | 11/1990 |
| EP | 1367392 | 5/2003 |
| EP | 1674866 | 8/2005 |

* cited by examiner

*Primary Examiner* — Gail Verbitsky
(74) *Attorney, Agent, or Firm* — McDonnell Boehnen Hulbert & Berghoff LLP (57) ABSTRACT

A method for checking the quality of thermal coupling between a measuring cell and a thermostatted element of an analyzer, where the measuring cell can be exchangeably inserted into an analyzer to measure at least one parameter of a sample, and is provided with at least one sensor element in a measuring channel.

14 Claims, 3 Drawing Sheets

METHOD FOR MONITORING THE THERMAL COUPLING OF A MEASURING CELL

CROSS-REFERENCE TO RELATED APPLICATIONS

This application claims priority to European Patent Application No. 08172121.9, filed Dec. 18, 2008, which is incorporated herein by reference in its entirety for all purposes.

BACKGROUND OF THE INVENTION

1. Field of the Invention

The invention relates generally to a method for monitoring a thermal coupling, and in particular, a thermal coupling between a measuring cell and a thermostatted element of an analyzer.

2. Description of Related Art

It is known that sensor elements of many measuring devices and analyzers have temperature-dependent signal properties. Depending on the particular type of sensor used, this temperature dependence is due to thermal influence on chemical processes, their equilibrium and/or their kinetics, or especially in the case of electrochemical sensors, is due to changes in the chemical-physical characteristics.

Such sensors are often used in medical analyzer systems for determining partial gas pressure, pH-value, or ion and metabolite concentrations in body fluids. In particular, such sensors are used in blood gas analyzers, used in medical diagnostics.

While the temperature coefficients of the sensors can be determined fairly easily by suitable calibration measurements, a problem arises in the measuring of blood gases and pH, in so far as the measured variables ($pO_2$, $pCO_2$, and pH) are temperature-dependent, and the temperature coefficients of the sample needed for computational correction are not known with sufficient precision. If the measured values obtained for a blood sample, for instance at room temperature, are to be computationally corrected to obtain values at body temperature (37° C.), the results will be imprecise.

In order to avoid the above mentioned temperature dependencies it is known to use sensors under controlled temperature conditions, i.e., in thermostats. When the measuring cells are to be exchanged after a certain period of use, the measuring cell and the thermostat, which is a fixed component of the analyzer, should be easily separable.

In general, the measuring cells are operated in a thermostatted chamber of the analyzer, which is kept at a constant temperature and is usually made of synthetic materials.

In order to optimally simulate the situation prevailing within the body of the patient, measurements are carried out at a sample temperature of 37° C. Even if only a short span of time elapses between the taking of the sample and the measurement, the blood sample will have cooled off significantly and usually will have to be rapidly reheated to body temperature in the measuring cell inside the analyzer.

For rapid and reproducible thermostatting it is essential to heat not only the media introduced into the measuring cell, such as calibrating media, control media, or sample fluids, to the required operating temperature in a fast and reproducible way, but also the sensors contained in the measuring cell.

A sensor device for measuring pH and blood gas parameters ($pCO_2$, and $pO_2$) described in U.S. Pat. No. 5,046,496 has the individual electrodes applied on a rectangular carrier plate of non-conductive ceramics by means of thick-film technology. The carrier plate with the measuring electrodes is glued into the housing of a flow-through cell. A temperature sensor and a heating element are also provided on the carrier plate in order to attain and control the temperature required for measurement.

A portable diagnosis system, in which the heating element is also directly integrated in the sensor chip with its individual electrodes, is known from U.S. Pat. No. 6,890,757 B2. In that system, the sensor chip is being monitored in a contact-free manner by an IR sensor for temperature measurement.

Finally, US Patent Application Publication No. 2003/0057108 A1 discloses a method for fast hydration and heating of chemical, electrochemical, and biochemical sensors. In that method the sensor cartridge consists of a lower part made of plastic, in which the sensors are provided, and of a metal cover plate, which can be used for heat transfer into the sensor cartridge. For this purpose the cover plate is in contact with suitable heating or cooling elements, for instance a Peltier element.

The additional expense incurred by integrating a heating element and a temperature measuring element into the measuring cell is a disadvantage of the above mentioned solutions.

An analyzer device with a thermostatted measuring cell having electrochemical electrodes is described in U.S. Pat. No. 7,491,175. In that analyzer device the measuring cell is thermostatted by Peltier elements, a flat, thermally conductive distributor element being placed between the Peltier elements and the wall of the measuring cell. This kind of thermostatting is equivalent to an air-bath on account of the unavoidable air gap, heat transfer mainly being limited by the thickness of the polymer material of low thermal conductivity surrounding the electrochemical sensor, and the remaining air gap against the thermostatted surface.

To improve heat transfer to the measuring cell, US Patent Application Publication No. 2006/0140822 disclosed a thermally conductive, elastic or plastic layer, which adheres at least in the contact area to a wall of the measuring cell or to the thermostatted supporting surface of the analyzer, and which can be removed without residue from the thermostatted supporting surface or the measuring cell wall, when the measuring cell is exchanged. US 2006/0140822 further proposed that the wall of the measuring cell, which carries one or more sensor elements on the inside facing the measuring channel, be made of a thermally conductive metal or metal alloy, at least in the contact area with the thermostatted supporting surface of the analyzer.

By such arrangements (thermally conductive layer or metal wall of the measuring cell), which can also be combined, heat transfer resistance between the heat source, the thermostatted supporting surface of the analyzer, and the sensor- or sample-plane is substantially minimized.

If the measuring cell is damaged or if the contact areas are considerably soiled, contact with the thermostatted surface is achieved only at a few points and in an irreproducible way, such that the quality of thermal coupling is degraded while the malfunction escapes quick detection.

As a consequence of insufficient thermal coupling temperature adaptation between sensor and sample is delayed. It will thus take longer to perform measurement at the desired target temperature, or the measuring is carried out prematurely, prior to reaching proper measuring temperature of 37° C., for instance.

Accordingly, the inventors have identified a need in the art to provide a method for checking the thermal coupling of a measuring cell inserted in an analyzer, which will avoid the use of a heating element and a temperature sensor in the measuring cell and permit rapid and reliable detection of any deterioration of thermal coupling when the measuring cell is exchanged, malfunctions or is in normal use.

SUMMARY OF THE INVENTION

It is against the above background that the present invention provides certain unobvious advantages and advancements over the prior art.

Although the present invention is not limited to specific advantages or functionality, it is noted that the present invention provides a method for checking the quality of thermal coupling between a measuring cell and a thermostatted element of an analyzer, the measuring cell being exchangeably insertable into the analyzer to measure at least one parameter of a sample, and being provided with at least one sensor element in a measuring channel. The method includes the following steps:
   a. establishing mechanical contact with between the measuring cell and the thermostatted element;
   b. filling the measuring channel with a fluid,
   c. equilibrating the temperature between the measuring channel and the fluid;
   d. applying a rapid temperature change using the thermostatted element;
   e. measuring over time a signal curve of the at least one sensor element after the rapid temperature change has been applied; and
   f. determining the quality of the thermal coupling by analyzing the signal curve over time resulting from the measurements of step (e).

In various aspects of the invention, the fluid is selected from a calibrating fluid, a rinsing fluid, a sample fluid and a quality control fluid. Also, the sensor element may be used for measuring the signal curve.

In further aspects of the invention, sensor may be a temperature dependent sensor, a chemical sensor or an optical sensor. Also, a signal curve of a temperature-dependent property of the fluid, such conductivity, resistance, or impedance of the fluid, may be measured.

In one particular embodiment of the method of the invention, a maximum difference D between a normalized temperature curve of the thermostatted element and a normalized conductivity, resistance or impedance curve is determined, and the quality of the thermal coupling is evaluated using a preselected threshold value for the maximum difference D.

In another particular embodiment, a quotient Q of a slope of a temperature curve of the thermostatted element and of a slope of a conductivity, resistance, or impedance curve of an operational fluid are determined and the quality of the thermal coupling is evaluated using a preselected threshold value for the quotient Q.

In further aspects of the invention, the sensor is an electrochemical sensor or an optical sensor element for determination of anions or cations; wherein the cations may be selected from $Li^+$, $Na^+$, $K^+$, $Mg^{++}$, and $Ca^{++}$, and the anions may be $Cl^-$.

Still further, the method of the invention may include the determination of biochemical substances, dissolved gases or pH value.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans will appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

Before describing the present invention in detail, a number of terms will be defined. As used herein, the singular forms "a", "an", and "the" include plural referents unless the context clearly dictates otherwise.

For rapid and reproducible thermostatting of the media and sensor elements contained in the measuring cell the quality of thermal coupling between the thermostatted element and the wall of the measuring cell is of decisive importance. Any air gap between thermostatted element and measuring cell or sensor cartridge, while usually not entirely avoidable, should remain within a narrow tolerance range.

Figure 1:
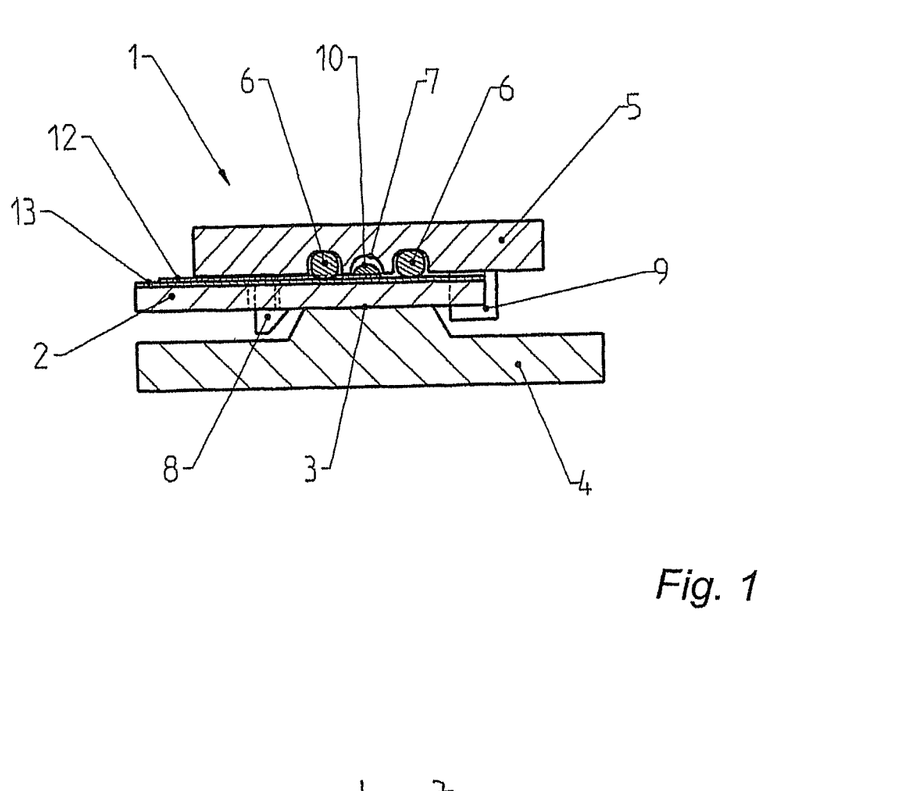
FIG. 1 shows a device for implementation of the method of the invention, for thermostatting a measuring cell that can be inserted into an analyzer, in a sectional view perpendicular to the flow direction of the sample.

In the one embodiment, the device for thermostatting a measuring cell 1 for insertion into an analyzer (not shown here in detail), which is presented in FIG. 1, has at least one planar measuring cell wall 2, which can be brought into contact with a thermostatted supporting surface 3 of the analyzer. The supporting surface 3 serves for the uniform transfer of heat energy supplied by a thermostatted element 4 (heating or cooling element, e.g., Peltier element).

In the embodiment of the invention shown in FIG. 1, the measuring cell 1 is configured as a two-part flow-through cell, through which the sample flows in a direction perpendicular to the plane of the drawing. The planar measuring cell wall 2 forms the lower part of the housing and is made of material with good thermal conductivity; together with a thermally insulating upper housing part 5 it bounds the measuring channel 7, sealing elements 6 being interposed. The two housing parts 2, 5 are connected by locking elements 8, 9. At least one sensor element 10, for instance an electrochemical sensor, is located in the measuring channel 7. In the example shown, the planar wall 2 of the measuring cell is made of metal or a metal alloy, such that good heat transfer to the sensor elements 10 and the sample in the measuring channel 7 is ensured. If electrochemical sensors are used the sensors and their conductive leads 12 carrying the sensor signals are placed on the wall 2 of the measuring cell with an electrically insulating layer 13 being interposed.

Thus, when the method of the present invention is applied the supporting surface 3 is heated or cooled by a heating or cooling element in a sudden manner.

Figure 2:
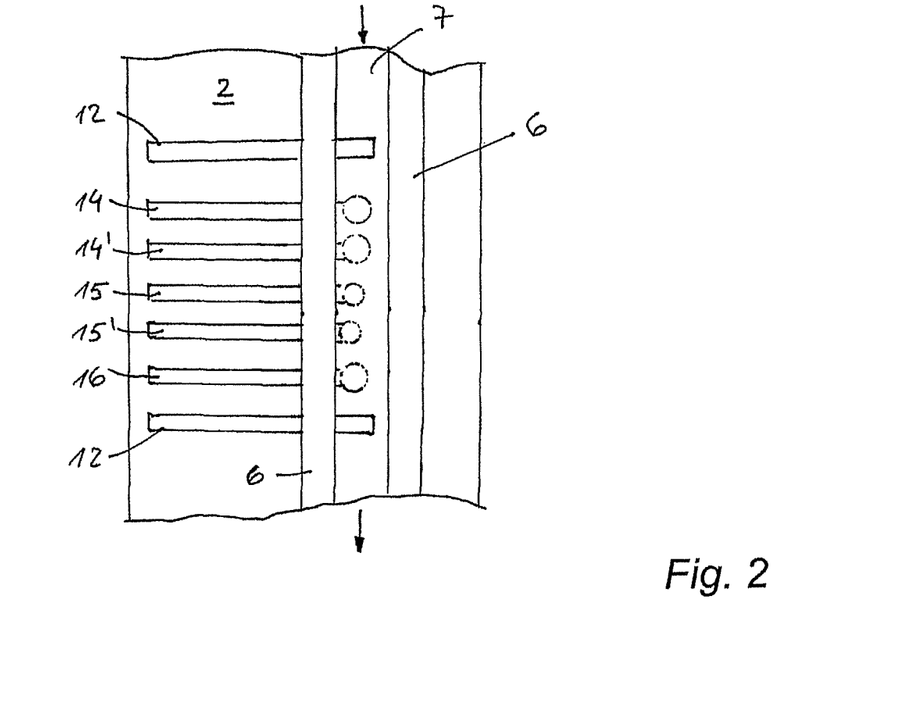
FIG. 2 shows a section of a measuring cell in the area of the measuring channel with conductive paths and sensor elements.

In one embodiment of the invention, the method of measuring electrical conductivity when determining the hematocrit of blood samples and computing the hematocrit from the measured conductivity of the blood samples, known from U.S. Pat. No. 4,686,479, is used to record the temperature-dependent change in conductivity of the fluid (e.g., sample, calibrating, quality control, or rinsing fluid) in the measuring channel 7. FIG. 2 further shows the conductive leads 12 for conductivity measurement, which are applied on the wall of measuring cell 2, with an electrically insulating layer interposed, and the leads 14, 14', 15, 15', and 16 for the measurement of $O_2$, $CO_2$, and pH-value.

The invention is suitable for an embodiment wherein the quality of thermal coupling between the wall 2 of the measuring cell and the supporting surface 3 of the thermostatted element 4 of the analyzer can be inferred from the diagram of the temperature kinetics, for instance by determining the maximum difference D between the normalized temperature curve Tn of the thermostatted element and the normalized conductivity curve Ln, or resistance or impedance curve, the quality of thermal coupling being evaluated by using a predetermined threshold value (e.g., 45%) for the maximum difference D. The difference signal is labelled $D_s$ in FIGS. 3 to 6.

In various embodiments, the normalized temperature curve Tn of the supporting surface (FIGS. 3 to 6) and the normalized signal curve Ln of the conductivity measuring electrodes (FIGS. 3 and 4) as well as the normalized signal curve Sn of the potassium electrode (FIGS. 5 and 6) were obtained in the two-step process.

In a first step all values $W_t$ of the measured curve were converted according to the formula $W_t' = (W_t/W_{t=0}) - 1$. In this instance W is the measured value, while t is the time of measurement.

In a second step all values $W_t'$ were normalized according to the formula $W_t'' = (W_t'/W_{t=120}') \cdot 100$ and were entered as curves into the diagrams of FIGS. 3 to 6.

The difference curves $D_s$ in the diagrams were obtained as differences of the two normalized curves.

Figure 3:
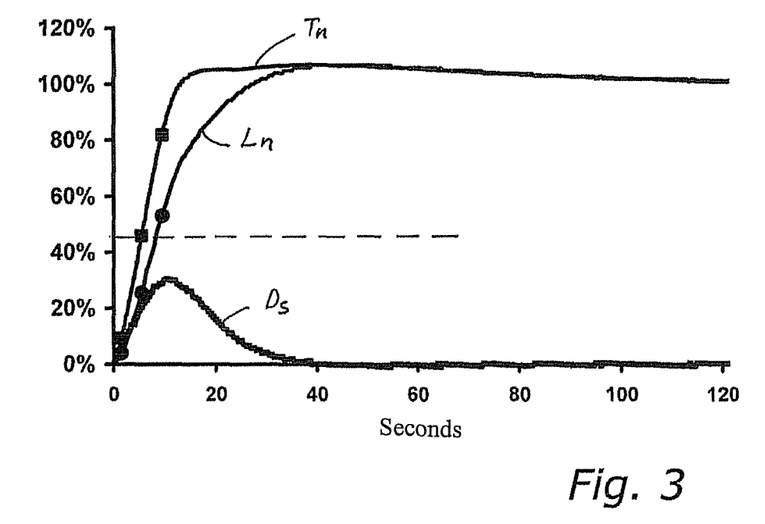
FIG. 3 shows normalized signal curves, in percent, of temperature $T_n$ of the thermostatted element of the analyzer and of conductivity $L_n$ of the fluid in the measuring channel, with a temperature jump having been applied, in a case of good thermal coupling.

FIG. 3 shows the kinetics of a thermal coupling of sufficient quality, which for instance can be seen from the fact that the maximum of the difference curve $D_s$ remains below the predetermined threshold, in this case 45%.

Figure 4:
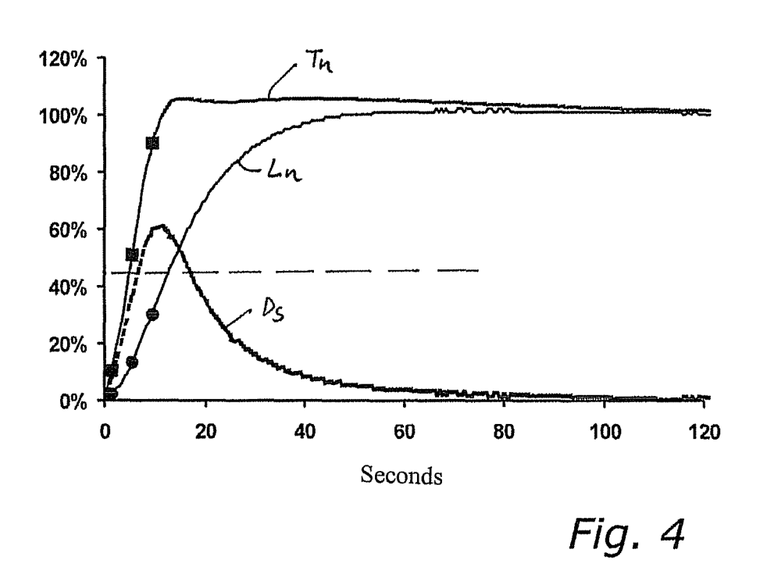
FIG. 4 shows normalized signal curves in percent, of temperature $T_n$ of the thermostatted element of the analyzer and of conductivity $L_n$ of the fluid in the measuring channel, with a temperature jump having been applied, in a case of degraded thermal coupling.

FIG. 4 shows the kinetics of a thermal coupling degraded by the presence of a hair on the supporting surface, which can be diagnosed by the maximum of the difference curve exceeding the predetermined threshold, in this case 45%.

In one embodiment of the invention, the temperature curve measured over time of the temperature-dependent quantity of the internal or external fluid is compared to the temperature curve over time of the thermostatted element. The respective measured curves may for instance be normalized and the time curve of their difference or quotient may be determined (see FIG. 3 to FIG. 6). Other methods of evaluating the time curve, for instance determination of time derivatives, may also be used.

When the method of the invention is applied, the temperature of the analyzer's supporting surface for the measuring cell is varied in a sudden manner by means of an analyzer-integrated heating element after the measuring cell has been filled with a liquid medium (calibrating medium, quality control medium, rinsing fluid, or sample fluid). Within a certain range, neither the amplitude nor the direction (heating or cooling) of the temperature jump is critical. In parallel with the temperature change the conductivity (or another quantity) is measured as a function of time, using the conductivity electrodes present in the measuring cell.

Using the kinetics of the conductivity change in response to the temperature jump applied by the analyzer the quality of the thermal coupling may be assessed from the slope of the measured curves or by evaluating a hysteresis-like parameter between temperature curve of the supporting surface and change in conductivity.

Since in various embodiments recording of a parameter correlating with the temperature and not the temperature itself is sufficient, sensor elements already present in the measuring cell may be used, for instance electrodes for determining the hematocrit value by measuring electrical conductivity in the blood sample, and the cost of additionally integrating a temperature sensor in the measuring cell may be avoided.

Besides electrodes for measuring conductivity, other sensor elements present in the measuring cell may be used according to various embodiments of the invention, for example electrochemical or optical sensors for measuring gas partial pressures (e.g. $PO_2$, $PCO_2$), or pH-value, or electrolytes ($Li^+$, $K^+$, $Na^+$, $Mg^{++}$, $Ca^{++}$, $Cl^-$), or metabolites (e.g., glucose, lactate, urea, creatinine) in body fluids, especially in blood samples.

In particular embodiments of the invention, sensor elements are electrochemical and optical sensors for determination of electrolyte values. Optical sensors use dyes, whose optical properties (e.g., absorption, luminescence) are temperature-dependent.

Electrochemical sensors for determination of electrolyte values are usually potentiometric electrodes. The difference in potential EMF (electromotive force) is measured between a reference electrode and an ion-selective measuring electrode. The EMF as a function of concentration [c] or rather activity [a] of the ion to be measured is given by Nernst's equation:

$$EMF = E_0 + 2.303\, RT/(zF) \log[a],$$

where R is the gas constant, T the absolute temperature, F Faraday's constant and z the charge number of the ion to be measured. From Nernst's equation it is obvious that the measured signal is temperature-dependent. Within physiological ranges of concentration the values of concentrations do not change with temperature, especially in the case of alkaline metal cations dissolved in aqueous fluids, while the potentiometric signal does change.

The concentration values of some metabolites, such as glucose or lactate, also do not change with temperature. In the particular embodiment, the measurement signal from the sensor element is typically temperature-dependent.

In various embodiments, in the sensor elements for the determination of gases, for instance blood gases, or of the pH-value, the measurement signal is usually influenced by a number of temperature-dependent quantities, for instance by processes within the sensor element and by the analyte value of the fluid.

In various aspects of the invention, waiting for temperature equilibration between internal or external fluid and the measuring channel may be performed, for instance, by waiting for a predefined length of time during which temperature equilibration can occur. In one aspect of the invention, the signal curve could also be measured and analyzed over time of a temperature-dependent characteristic of the internal or external fluid, or the signal curve could be measured over time of a temperature-dependent, electrochemical or optical sensor element, and the onset of thermal equilibrium between internal or external fluid and the measuring channel be determined from the signal curve. This can be accomplished by waiting until there is no longer any substantial change in the signal curve.

The electrical conductivity of operational fluids (calibrating fluids, rinsing fluids, quality control fluids) and of the sample (blood) is temperature-dependent in case of blood gas analyzers. The gas partial pressures ($PO_2$ and $PCO_2$) and the pH-value are also temperature-dependent. The concentrations to be measured, in particular ion and metabolite concentration, are not temperature-dependent as a rule. Over a large range at least their temperature dependence is so low that it need not be taken into account. In these cases the temperature dependence of the electrochemical or optical sensor element itself may be used.

The sensor elements already present in the measuring cell for sample measurement may used for obtaining the signal curve over time. This will provide completely automated and thus economical checking of thermal coupling of the sensor cartridge by means of sensing devices already present.

Another aspect of the invention is directed to checking of thermal coupling carried out by measuring the signal curve over time of conductivity, resistance or impedance (or a parameter derived therefrom) of the operational fluid.

In one aspect, the sensor is an electrochemical sensor or an optical sensor element for determination of anions or cations; wherein the cations may be selected from $Li^+$, $Na^+$, $K^+$, $Mg^{++}$, and $Ca^{++}$, and the anions may be $Cl^-$. In the fluids used, for instance calibrating or quality control fluids, these substances are present as dissolved salts (LiCl, NaCl, KCl, $MgCl_2$, $CaCl_2$).

A conductivity measurement, wherein the "sensor elements" are simple electrical contacts in the measuring channel and the sensor elements by themselves show no appreciable temperature dependence (in a first approximation) may be used in the method of the invention. The measurement variable itself, i.e., the electrical conductivity of the fluid in the measuring channel, varies essentially in a way proportional to temperature, such that the signal curve over time is directly correlated with temperature (i.e., without delay).

Still further, the invention includes chemical sensors wherein the temperature-dependent changes of the concentrations of the substances to be determined may be superimposed on the signal curve. If, for example, the sensor is not at equilibrium with the substance to be determined at a certain temperature, waiting for a certain response time will be necessary.

It is also possible to measure the signal curve over time of the measurement signal of an electrochemical or optical sensor element within the measuring chamber for determining a substance contained in the sample fluid, which element is in contact with the internal or external fluid, after applying a sudden temperature change.

Further aspect of the invention is directed to sensor elements that are electrochemical or optical sensor elements for determining biochemical substances in a sample, such as glucose, lactate, urea, or creatinine. These sensor elements can be used if none of the above-mentioned sensor elements are present in the measuring cell.

Still further, the invention is directed to electrochemical or optical sensor elements for determining gases dissolved in a sample, e.g., oxygen and carbon dioxide, or electrochemical or optical sensor elements for determining pH. Such sensor elements differ from the initially mentioned sensor elements in so far as the sensor elements themselves and characteristic variables of the substances dissolved in the fluid, such as their partial pressures or $H^+$-ion concentrations, are temperature-dependent.

EXAMPLES

Example 1

Conductivity Measurement

In one embodiment, the determination of the maximum difference D between the temperature curve T(t) of the supporting surface and the conductivity curve L(t) of the fluid contained in the measuring cell (FIGS. 3 and 4) is carried out as follows:

$$D=\max\left[(T(t)-T(s))/(Te-Ts)-(L(t)-L(s))/(Le-ls)\right]<0.45 \quad (1)$$

T(t) is temperature as a function of time;
Ts is starting temperature before T-jump;
Te is end temperature after T-jump;
L(t) is conductivity as a function of time;
Ls is conductivity before T-jump; and
Le is conductivity after T-jump.

"Max" means that for computing D according to equation (1) temperature T(t) and conductivity L(t) are measured at the time t at which the difference signal D in FIG. 3 or 4 reaches a maximum. This point in time can, for instance, be determined directly by analyzing the curve of the difference signal as shown in the diagrams of FIG. 3 or 4.

In another embodiment, D may be determined by computing via equation (1) a sequence of test values for D from value pairs T(t) and L(t) obtained over a period of time, and setting D equal to the greatest of these test values.

The maximum of the difference curve shown in FIG. 3 occurs at 10.5 seconds. From the raw data for T and L presented in Table 1 the value 0.31 for D is obtained by equation (1). This value is smaller than the predetermined threshold value 0.45 (or 45%). Thus the thermal coupling of the measuring cell in this example is satisfactory.

TABLE 1

| T(t = 10.5 s) | Ts | Te | L(t) | Ls | Le | D |
|---|---|---|---|---|---|---|
| 36.3 | 30.0 | 37.0 | 823 | 763 | 865 | 0.31 |

The maximum of the difference curve of FIG. 4 is located at 11.0 seconds. With the raw data for T and L shown in Table 2 equation (1) delivers a value of 0.61 for D. This value is greater than the predetermined threshold value of 0.45 (or 45%). Thus thermal coupling in this example is not satisfactory.

TABLE 2

| T(t = 11 s) | Ts | Te | L(t) | Ls | Le | D |
|---|---|---|---|---|---|---|
| 36.9 | 30.0 | 37.0 | 782 | 746 | 843 | 0.61 |

Example 2

Evaluation of the Quality of Thermal Coupling by Conductivity Measurement

In the particular embodiment, the evaluation of the quality of thermal coupling is carried out by determining the difference in curvature of the rising slope of the temperature curve of the supporting surface of the thermostatted element and of the rising slope of the conductivity-, resistance- or impedance curve of the operational fluid as a quotient Q, and by judging the quality of thermal coupling by comparing the quotient Q with a preselected threshold value.

The quotient Q may, for instance, be obtained from the formula:

$$Q = \frac{(T_2 - T_1)/(T_3 - T_2)}{(L_2 - L_1)/(L_3 - L_2)} \quad (2)$$

where $T_1$, $T_2$, $T_3$ denote the temperature of the supporting surface of thermostatted element at predetermined times $t_1$, $t_2$, $t_3$ and $L_1$, $L_2$, $L_3$ denote the conductivity, resistance, or impedance of the internal or external fluid at the predetermined times $t_1$, $t_2$, $t_3$.

From the raw data for T and L shown in Table 3 and measured at the times t1=0.5 s, t2=4.5 s, t3=8.5 s, equation (2) delivers a value of 1.26 for Q. This value is less than the predetermined threshold of 1.5. Thus the thermal coupling of the measuring cell is satisfactory.

TABLE 3

| $T_1$ | $T_2$ | $T_3$ | $L_1$ | $L_2$ | $L_3$ | Q |
|---|---|---|---|---|---|---|
| 30.3 | 32.6 | 35.3 | 764 | 783 | 811 | 1.26 |

From the raw data for T and L shown in Table 4 and measured at the times t1=0.5 s, t2=4.5 s, t3=8.5 s, equation (2) delivers a value of 1.79 for Q. This value is greater than the predetermined threshold of 1.5. Thus the thermal coupling of the measuring cell in this example is not satisfactory.

TABLE 4

| $T_1$ | $T_2$ | $T_3$ | $L_1$ | $L_2$ | $L_3$ | Q |
|---|---|---|---|---|---|---|
| 30.3 | 32.9 | 35.8 | 747 | 755 | 771 | 1.79 |

In another embodiment, the evaluation of the quality of thermal coupling between the measuring cell wall 2 and the supporting surface 3 of the thermostatted element 4 of the analyzer is carried out by analyzing the temperature kinetics, for instance by determining the maximum difference D between the normalized temperature curve of the thermostatted element and the normalized value of the measuring signal of an ion-selective electrode, e.g., a potassium-selective electrode, and judging the quality of thermal coupling by comparing D with a predetermined threshold (for instance 20%).

Example 3

Potentiometric Measurement

In the particular embodiment, the determination of maximum difference D between the temperature curve T(t) of the supporting surface and the curve of the measurement signal S(t) of a sensor element present in the measuring cell (FIGS. 5 and 6) is carried out as follows:

$$D = \max\ [(T(t)-Ts)/(Te-Ts)-(S(t)-Ss)/(Se-Ss)] < 0.45 \quad (3)$$

T(t) is temperature as a function of time;
Ts is starting temperature before T-jump;
Te is end temperature after T-jump;
S(t) is measurement signal of potassium electrode as a function of time;
Ss is measurement signal of potassium electrode before T-jump; and
Se is measurement signal of potassium electrode after T-jump.

Figure 5:
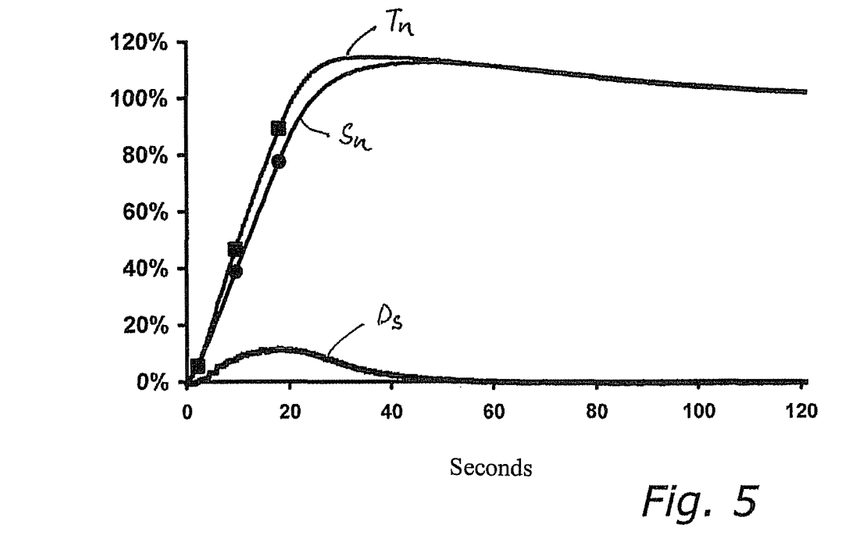
FIG. 5 shows normalized signal curves, in percent, of temperature $T_n$ of the thermostatted element and of the measuring signal $S_n$ of an electrochemical (potentiometric) potassium sensor (comprising a measuring electrode and a reference electrode) in contact with a potassium-containing internal or external fluid, with a temperature jump having been applied, in a case of good thermal coupling.
Figure 6:
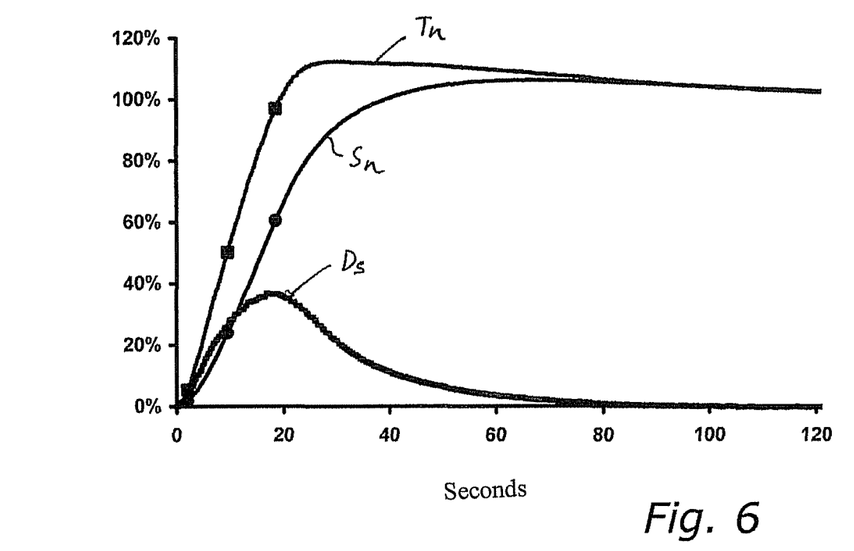
FIG. 6 shows normalized signal curves in percent, of temperature $T_n$ of the thermostatted element and of the measuring signal $S_n$ of an electrochemical (potentiometric) potassium sensor (comprising a measuring electrode and a reference electrode) in contact with a potassium-containing internal or external fluid, with a temperature jump having been applied, in a case of degraded thermal coupling.

"Max" means that for computing D according to equation (3) temperature T(t) and signal value S(t) of the electrode are measured at the time t at which the difference signal D in FIG. 5 or 6 attains a maximum. This point in time can for instance be determined directly by analyzing the curve of the difference signal as shown in FIG. 5 or 6.

In another embodiment, D may be determined by computing via equation (3) a sequence of test values D from value pairs T(t) and S(t) obtained over a period of time, and setting D equal to the greatest of these test values.

The maximum of the difference curve shown in FIG. 5 occurs at 14.5 seconds. From the raw data for T and S presented in Table 5 the value 0.12 for D is obtained by equation (3). This value is less than the predetermined threshold value 0.25 (or 25%). Thus the thermal coupling of the measuring cell is satisfactory.

TABLE 5

| T(t = 14.5 s) | Ts | Te | S(t) | Ss | Se | D |
|---|---|---|---|---|---|---|
| 36.3 | 30.1 | 37.0 | 987 | 1076 | 962 | 0.12 |

The maximum of the difference curve of FIG. 6 is located at 17.0 seconds. With the raw data for T and S shown in Table 6 equation (3) delivers a value of 0.36 for D. This value is greater than the predetermined threshold value of 0.25 (or 25%). Thus thermal coupling in this example is not satisfactory.

TABLE 6

| T(t = 17 s) | Ts | Te | S(t) | Ss | Se | D |
|---|---|---|---|---|---|---|
| 36.9 | 30.1 | 37.0 | 1007 | 1076 | 965 | 0.36 |

Example 4

Evaluation of the Quality of Thermal Coupling by Potentiometric Measurement

In the particular embodiment, the evaluation of the quality of thermal coupling may also be carried out by determining the difference in curvature of the rising slope of the temperature curve of the supporting surface of the thermostatted element and of the rising slope of the measurement signal of the potentiometric sensor as a quotient Q, and by judging the quality of thermal coupling by comparing the quotient Q with a preselected threshold value.

The quotient Q may for instance be obtained from equation (4):

$$Q = \frac{(T_2 - T_1)/(T_3 - T_2)}{(S_2 - S_1)/(S_3 - S_2)} \quad (4)$$

where $T_1$, $T_2$, $T_3$ denote the temperature of the supporting surface of the thermostatted element at predetermined times $t_1$, $t_2$, $t_3$ and $S_1$, $S_2$, $S_3$ denote the measurement signal of an potentiometric sensor at the predetermined times $t_1$, $t_2$, $t_3$.

From the raw data for T and S shown in Table 7 and measured at predetermined times t1=0.5 s, t2=4.5 s, t3=8.5 s, equation (4) delivers a value of 1.14 for Q. This value is less than the predetermined threshold of 1.20. Thus the thermal coupling of the measuring cell is satisfactory.

TABLE 7

| $T_1$ | $T_2$ | $T_3$ | $S_1$ | $S_2$ | $S_3$ | Q |
|---|---|---|---|---|---|---|
| 30.1 | 31.4 | 32.9 | 1074 | 1058 | 1037 | 1.14 |

From the raw data for T and S shown in Table 8 and measured at predetermined times t1=0.5 s, t2=4.5 s, t3=8.5 s, equation (4) delivers a value of 1.34 for Q. This value is greater than the predetermined threshold of 1.20. Thus the thermal coupling is not satisfactory.

TABLE 8

| $T_1$ | $T_2$ | $T_3$ | $S_1$ | $S_2$ | $S_3$ | Q |
|---|---|---|---|---|---|---|
| 30.1 | 31.4 | 33.1 | 1076 | 1068 | 1054 | 1.34 |

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A method for checking a quality of a thermal coupling between a measuring cell and a thermostatted element of an analyzer, the measuring cell being exchangeably insertable into the analyzer, and being provided with at least one sensor element in a measuring channel, the method comprising:
    (a) establishing mechanical contact with between the measuring cell and the thermostatted element;
    (b) filling the measuring channel with a fluid having a known temperature dependent property,
    (c) equilibrating the temperature between the measuring channel and the fluid;
    (d) applying a rapid temperature change to the measuring channel using the thermostatted element;
    (e) measuring over time a signal curve of the at least one sensor element after the rapid temperature change has been applied, wherein the at least one sensor element measures the signal curve over time of the temperature dependent property of the fluid, and
    (f) determining the quality of the thermal coupling by analyzing the signal curve over time resulting from the measurements of step (e).

2. The method of claim 1, wherein the fluid is selected from a calibrating fluid, a rinsing fluid, a sample fluid and a quality control fluid.

3. The method of claim 1, wherein the at least one sensor element is used for measuring the at least one parameter of a sample to be analyzed.

4. The method of claim 1, wherein the at least one sensor element measures the signal curve of electrical conductivity, resistance, or impedance of the fluid.

5. The method of claim 1, wherein the sensor element does not determine the temperature of the fluid.

6. A method for checking a quality of a thermal coupling between a measuring cell and a thermostatted element of an analyzer, the measuring cell being exchangeably insertable into the analyzer, and being provided with at least one sensor element in a measuring channel, the method comprising:
    (a) establishing mechanical contact with between the measuring cell and the thermostatted element;
    (b) filling the measuring channel with a fluid having a known temperature dependent property,
    (c) equilibrating the temperature between the measuring channel and the fluid;
    (d) applying a rapid temperature change to the measuring channel using the thermostatted element;
    (e) measuring over time a signal curve of the at least one sensor element after the rapid temperature change has been applied, wherein the at least one sensor element is a temperature dependent electrochemical sensor element or a temperature dependent optical sensor element, and
    (f) determining the quality of the thermal coupling by analyzing the signal curve over time resulting from the measurements of step (e).

7. The method of claim 6, wherein the at least one sensor element is an electrochemical sensor or an optical sensor element for determination of anions or cations in the fluid.

8. The method of claim 7 wherein the cations are selected from $Li^+$, $Na^+$, $K^+$, $Mg^{++}$, and $Ca^{++}$.

9. The method of claim 7, wherein the anions are $Cl^-$.

10. The method of claim 6, wherein the at least one parameter of the sample is a biochemical substance and the at least one sensor element is used for the determination of the biochemical substance.

11. The method of claim 6, wherein the at least one parameter of the sample is a dissolved gas or a pH value and the at least one sensor element measures the dissolved gases or the pH value.

12. The method of claim 6 wherein the sensor element does not determine the temperature of the fluid.

13. The method of claim 6, wherein the fluid is selected from a calibrating fluid, a rinsing fluid, a sample fluid and a quality control fluid.

14. The method of claim 6, wherein the at least one sensor element is used for measuring the at least one parameter of a sample to be analyzed.

* * * * *